United States Patent [19]

Parker

[11] Patent Number: 5,137,691

[45] Date of Patent: * Aug. 11, 1992

[54] ANTIBODY TESTING SYSTEM WITH REMOVABLE AIR GAP

[75] Inventor: James E. Parker, Long Beach, Calif.

[73] Assignee: V-Tech, Inc., Pomona, Calif.

[ * ] Notice: The portion of the term of this patent subsequent to Jan. 10, 2006 has been disclaimed.

[21] Appl. No.: 361,987

[22] Filed: Jun. 5, 1989

Related U.S. Application Data

[63] Continuation-in-part of Ser. No. 229,455, Aug. 8, 1988, abandoned, which is a continuation-in-part of Ser. No. 6,874, Jan. 27, 1987, Pat. No. 4,797,260.

[51] Int. Cl.$^5$ ............................................. G01N 21/01
[52] U.S. Cl. ........................................ 422/58; 422/69; 422/101; 422/104; 435/301
[58] Field of Search .................................. 422/55–58, 422/69, 100–104; 435/805, 301

[56] References Cited

U.S. PATENT DOCUMENTS

| | | | |
|---|---|---|---|
| 4,789,526 | 12/1988 | Matkovich | 422/101 |
| 4,797,259 | 1/1989 | Matkovich et al. | 435/7 |
| 4,797,260 | 1/1989 | Parker | 422/101 |
| 4,874,691 | 10/1989 | Chandler | 422/101 |
| 4,908,319 | 3/1990 | Smyczek et al. | 422/103 |

*Primary Examiner*—Timothy M. McMahon

[57] ABSTRACT

A device for performance of ligand-receptor assay methods for determining the presence of a ligand. The preferred ligand-receptor pair are antigen-antibody pairs. The device has a membrane having the receptor physically bound to its surface. A closable gap exists between the membrane and an absorbent means. Substantially all of the top surface of the membrane is exposed. The device has a piston means disposed inside the body member, and in air-tight seal with the body member. Means to actuate the piston means are disposed outside the body member. The piston means creates a region of reduced pressure.

10 Claims, 1 Drawing Sheet

ANTIBODY TESTING SYSTEM WITH REMOVABLE AIR GAP

This application is a continuation-in-part of U.S. patent application Ser. No. 07/006,874 filed Jan. 27, 1987, now U.S. Pat. No. 4,797,260 which disclosure is herein incorporated in full, and U.S. patent application Ser. No. 07/229,455, filed Aug. 8, 1998 now abandoned which disclosure in herein incorporated in full.

BACKGROUND OF THE INVENTION

1. Field of the Invention

This invention relates to apparatus and methods for testing for the presence of antigens using antibodies.

2. Prior Art

Valkirs et al disclose in U.S. Pat. No. 4,727,019 a device having a body member that contains a porous mass. A membrane having a ligand-receptor is disposed above the porous mass. The sample solution flows into the porous mass by capillary action only. There is no teaching of any means to reduce pressure to facilitate more rapid liquid transfer.

In U.S. Pat. No. 4,090,850 issued to Chan, an antibody coated cellulose paper is used in radioimmunoassays in conjunction with the test apparatus comprising a receptacle tray with multiple wells. Each of said wells having at its bottom an orifice such that the multiple wells can be simultaneously evacuated by a single source of reduced pressure.

In U.S. Pat. No. 3,888,629 issued to Bagshawe, a reaction cell for the performance of radioimmunoassay determinations and the like is disclosed. Here two halves of the cell are joined together, separated by a membrane containing the necessary antibodies to form a particulate reaction product. The liquid reagents flow through the membrane under the influence of gravity.

U.S. Pat. No. 4,424,279 issued to Bohn discloses an immunoassay apparatus having a cylindrical tube that has a plunger filter assembly slideably fitted therein. The filter is dome shaped and contains beads sensitized with immunologically reactive material.

Greenspan U.S. Pat. No. 4,189,385 discloses a method and apparatus for separating serum or plasma from the formed elements of blood. The apparatus disclosed is generally similar to that of Bohn, except instead of a filter, a one way valve is disclosed.

In Buono U.S. Pat. No. 4,057,499, another apparatus for the separation of blood is taught. The apparatus is similar to the apparatus disclosed in Bohn and Greenspan. The one way valve of Greenspan is a filter, but unlike the filter in Bohn, it contains no immunologically reactive material.

Moore et al. U.S. Pat. No. 3,870,639 teaches yet another similar blood plasma separation device. Other filtration devices include U.S. Pat. No. 4,522,713 to Nussbaumer and U.S. Pat. No. 3,687,246 to Spinosa.

Bohn, Greenspan, and Buono rely on a slight pressure differential being created when a plunger portion is forced into contact with fluid contained in an outer tube. The fluid beneath the plunger filter or valve is then forced upwardly into a receiver tube fitted within the outer tube.

A problem with prior testing devices is that an analytical laboratory, complete with vacuum lines is required to use the devices. It would be advantageous to have a device that requires no external source of vacuum. The present invention provides an externally manipulable piston for creating a region of reduced air pressure beneath a membrane binding an analytic compound, preferably an antibody. The region of reduced pressure causes the fluid to be tested to be rapidly drawn through the membrane.

Another problem with prior art devices has been that much of the sample never contacts the receptor site. Tests with increased sensitivity would result if all the sample contacted the receptor region.

Our popular structure for immunotesting devices is an immunoactive substrate bound to a membrane which lies upon an absorbent body. These embodiments do not feature an air gap. Typical prior art devices using this approach are shown in U.S. Pat. No. 4,632,901 and 4,727,019 both issued to Valkirs and U.S. Pat. No. 4,366,241 issued to Tom.

If a biological sample provides large enough amounts of analyte and the analyte and the immunoactive substrate react rapidly enough, then such devices are satisfactory. However, many times the analyte is found only in minute quantities or the analyte and the immunoactive substrate react slowly.

In cases like this it would be advantageous to have a different configuration of the immunotesting device. Such a configuration would allow sufficient time for the analyte and the immunoactive substrate to react.

SUMMARY OF THE INVENTION

A device for performance of ligand-receptor assay methods for determining the presence of a ligand. The preferred ligand-receptor pair are antigen-antibody pairs. The device has a membrane having the receptor physically bound to its surface. A closable gap exists between the membrane and an absorbent means. Substantially all of the top surface of the membrane is exposed. The device has a piston means disposed inside the body member, and in air-tight seal with the body member. Means to actuate the piston means are disposed outside the body member. The piston means creates a region of reduced pressure.

An aspect of this invention is:

A device for performing immunoassays comprising:

an immunosorbent membrane;

a means for absorbing liquid, said immunosorbent membrane disposable in a first position above said means for absorbing liquid, thereby creating an air gap, and disposable in a second position substantially contacting said means for absorbing liquid;

a means for moving from said first position to said second position; and a means for supporting said immunosorbent member and said means for absorbing liquid allowing liquid to be drawn through said immunosorbent member and into said means for absorbing liquid.

A further aspect of this invention is:

A device for performing immunoassays comprising:

an immunosorbent means;

a means to allowing incubation of the immunosorbent and a sample solution;

a means for drawing off the sample solution; and a special remaining in constant relationship with the immunosorbent means.

DETAILED DESCRIPTION OF THE INVENTION

As used herein "immunosorbent membrane" means porous material having an affinity to bind a pair of an antibody:antigen pair. In particular the porous material is a thin disk of material such as nitrocellulose.

As used herein "analyte solution" refers to an aqueous solution.

As used herein "analyte" refers to any material that can be involved in an antibody:antigen reaction. Typically the analyte will be an antigen, for example, a protein, a carbohydrate, cell walls, and small molecule haptens. It is possible that the analyte be an antibody that reacts with a bound antigen or an antibody to the antibody.

As used herein "immunoactive substrate" refers to a member of an antibody:antigen pair that can be non-diffusively bound to a porous support membrane.

As used herein "immunosorbent membrane" refers to a porous support membrane having an immunoactive substrate non-diffusively bound to it.

As used herein "absorbent material" refers to any material that absorbs liquid. The material can be a momolithic solid, such as cellulose acetate, or Porex ®, or it can be a granular solid desiccant. The preferred desiccant is a mixture of granular powdered desiccant, drierite ® (trademark for anhydrous calcium sulfate) and granular powdered absorbent, such as celite ® (trademark for diatomaceous earth). It is preferred that the absorbent material be able to absorb as much liquid as possible.

As used herein the word "user" refers to the person performing the immunoassay using the invention. The user can be a laboratory technician, but can be anyone in the case of home test kits. It is possible that the device disclosed herein could be used as part of an automated testing system then the "user" of the immunoassay device would be the automated system.

As used herein the word "ligand" is a compound or biological material whose presence is being determined. Examples include small molecules, such as cocaine, morphine, or progesterone; medium molecules, such as LHRH; large molecules, such as DNA, or LCG; and other biological materials, such as bacterial cell walls, viruses and the like.

As used herein, the word "receptor" is a compound or biological material that binds to a ligand. Preferred receptors are antibodies, including both polyclonal and monoclonal antibodies. The term also includes the active portion, or FAB fragment of antibodies, if it has been cleaved from the rest of the molecule.

As used herein the term "sample solution" is a solution that is suspected of containing a particular ligand. It is realized that a sample solution will frequently contain no ligand, or, in other words, the test for that ligand is negative.

Figure 1:
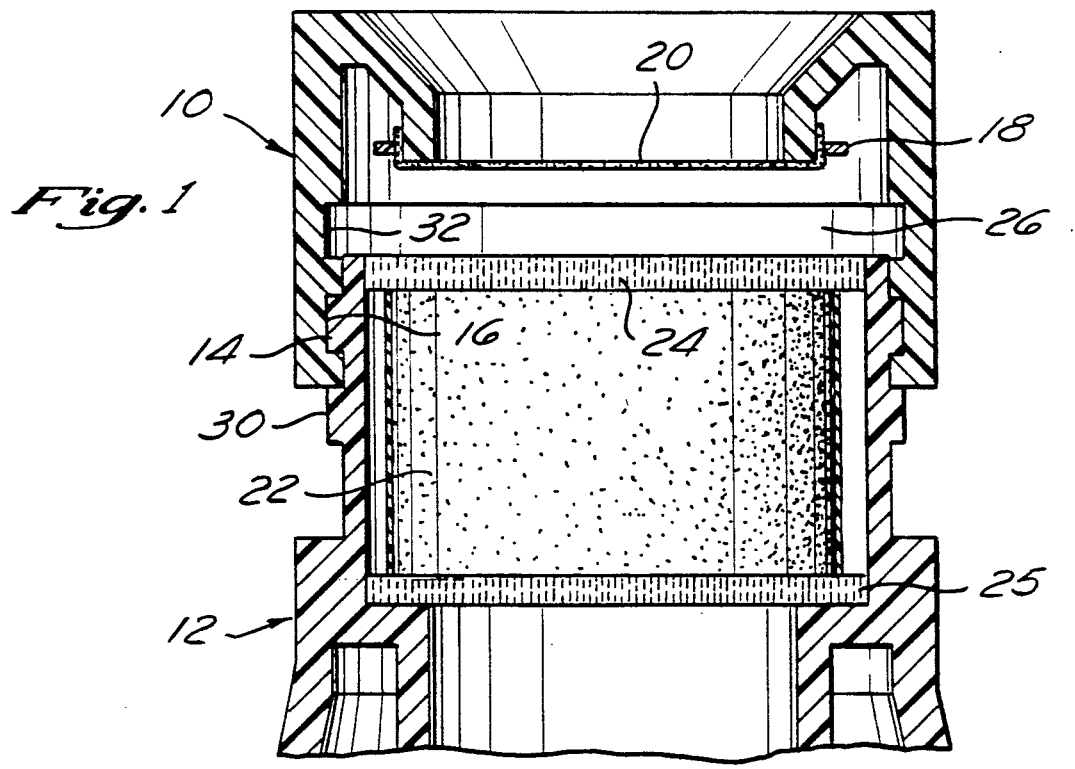
FIG. 1 is a cut away side view of a embodiment of this invention.

Referring now to FIG. 1, a cap member 10 is mated to a body member 12 by engaging a first snap ring 14 with a first snap ring receiver 16. A retaining ring 18 is friction fit within the cap, thereby securely retaining the immunosorbent membrane 20.

A mass of absorbent material 22 is disposed within the body cavity. The preferred absorbent material is a mixture of Celite and Drierite in powder form. A first retaining screen 24 holds the powdered absorbent material in place until use. There is an air gap 26 between the first retaining screen and the immunosorbent member. A second retaining screen 25 supports the absorbent material 22.

In use, the cap member 10 is pushed downwardly, snapping into a down position, thereby contacting the membrane with the first retaining screen 24. The body has a second snap ring 30 that mates with the first snap ring receiver 32 in the down position. The first snap ring mates with a second snap ring 14 receiver 32 on the cap.

A funnel-filter can be attached to the sample well in the cap, and is removed when the cap is depressed.

Figure 2:
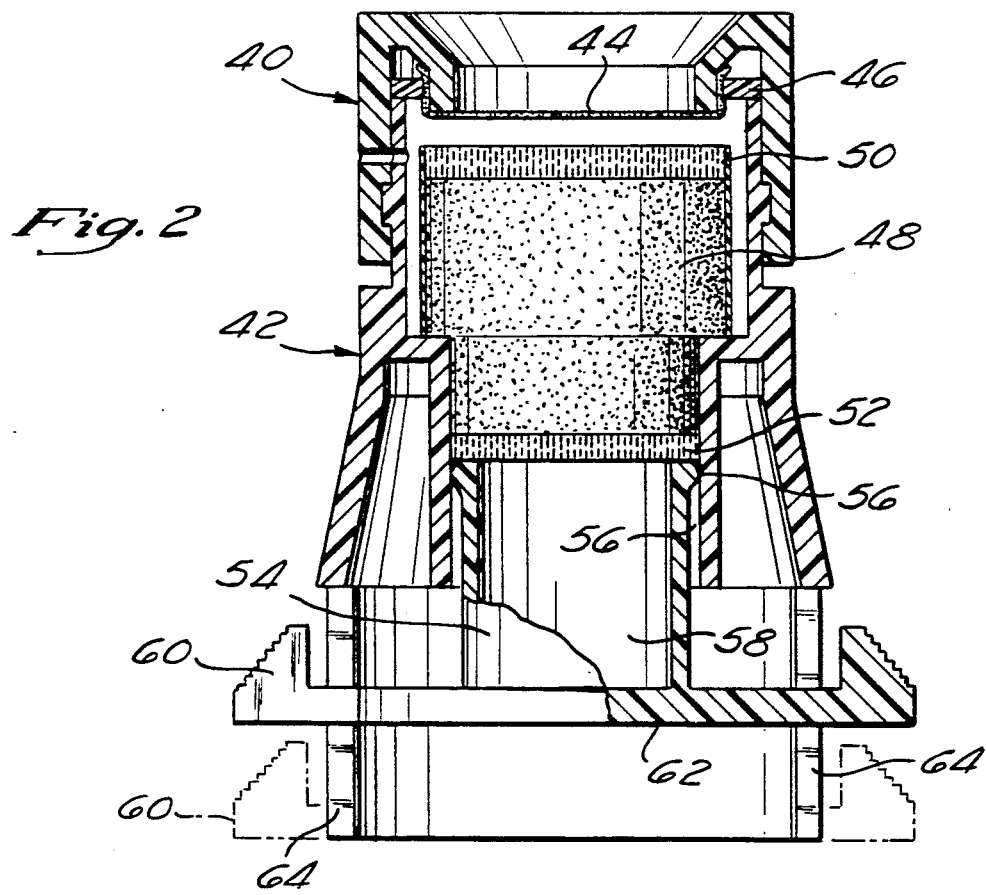
FIG. 2 is a cut away side view of a second embodiment of this invention.

Referring to FIG. 2, a cap 40 has been snap fit to a body member 42. An immunosorbent membrane 44 is secured by a retaining ring 46.

A mass of absorbent material 48 is disposed within the body cavity. A retaining screen 50 keeps the absorbent material in place within the body cavity. An optional lower retaining screen 52 is shown supporting the absorbent material. Without the lower retaining screen, the powder will settle into a relief housing a piston 54. The piston is disposed within the body at less than the uppermost possible position. In use, after the sample has incubated for the appropriate amount of time. The piston is moved to its uppermost position, thereby contacting a first retaining screen 50 with the immunosorbent membrane. The piston can then be drawn downwardly, thereby drawing liquid with it.

Absorbent material is supported on the second retaining screen. The second retaining screen is porous enough to allow the vacuum to draw liquid, but not porous enough allow the particulate absorbent material to flow through. The second retaining screen is disposed above a piston housing 56 and is in vacuum communication with the piston housing. That is, if the piston is depressed, a zone of reduced air pressure is created that acts directly on the bottom surface of the second retaining screen. Within the piston housing, the piston member 54 is sealingly engaged with the walls of the piston housing by a gasket means 56. Preferably, the top of the circumferential wall terminates in a peripheral lip extending outwardly, which engages the walls of the piston housing as the gasket means. In a preferred embodiment the piston has a piston wall forming a central well 58. The central well can accumulate liquid reagents or washing fluids used during the test for the ligand. Piston handles 60 attached to the piston base plate 62 extend through a slot 64 allowing external manipulation of the piston by the user. The piston handles are oppositely disposed on the piston base plate.

In an alternative embodiment, a first and second snap ring receiver are modeled into the cup, but only one snap ring is molded onto the body. The cup ring engages the first snap ring receiver in the upper position and the second snap ring receiver in the lower position.

In the use of this device, the sample is placed in contact with the immunosorbent membrane. After an optimum, predetermined incubation period has past, the handles are moved upwardly which allows the first retaining screen to contact the immunosorbent membrane, thereby drawing the liquid downwardly. If additional suction is required, the handles can be moved downwardly, creating a region of reduced air pressure which draws liquids through the membrane more effectively than without. The liquid will then be in the gap on the absorbent material retainer. The liquid will flow through in the retaining disk and into the absorbent powder.

The immunosorbent membrane can be made of any material that is conventionally used to bind proteins or antibodies. Examples include nitrocellulose membranes and the like. The absorbent material support disk can be made of any material that is porous enough to communicate a vacuum from the piston to the absorbent material. Examples include filter material, cellulose, cellulose acetate, Porex ®, and the like.

It is preferred that the body member, the cap, the piston the retaining cup and the absorbent material retaining disk all be made of moldable plastic. Such construction provides low cost components that are easily assembled. The gasket member of the piston wall has superior wall engagement properties when made of molded plastic.

The sample concentrator funnel allows the sample solution to pass only through the receptor site on the membrane. The analyte in the sample has a greater chance of reacting with the receptor site if all the sample solution passes through the receptor site, thereby significantly enhancing the sensitivity of the test.

The sample concentrator funnel 66 sits snugly within the funnel of the top of the cap member. The fit between the concentration funnel and the cap can be enhanced with engagement members formed when the plastic cap is formed. It is preferable, but not mandatory, that a filter member cover the bottom of the sample concentrator funnel. Then more contaminated samples, such as essentially untreated biological samples, can be run through the test apparatus. Examples of such fluids include blood serum, urine, and the like.

The sample essentially all contacts the receptor site which covers the exit from the concentrator funnel. After the sample has contacted the active zone, the sample concentrator funnel is removed and a test verification sample contacts the entire surface of the membrane. The test verification bone does not need the increased sensitivity provided by the sample concentrator funnel.

The porous member is granular desiccant. Examples of suitable desiccants include silica gel, calcium chloride and the like. During manufacture, the desiccant is packed into the body member having the vacuum plunger in the up position. The desiccant will absorb water from the reagents placed on the membrane. When needed the plunger is moved downwardly, urging the reagents through the membrane. Although the desiccant is shown extending to the bottom of the piston member, it need not extend that far. A retaining screen can be provided that supports the absorbent material.

One advantage to the use of desiccant as absorbant material is that no extra packets of desiccant need to be added to the shipping package. Such packages of desiccant are needed when convention absorbent, for example, cellulose nitrate are used.

A further advantage is that desiccant can absorb as much as five times the amount of liquid that a conventional absorbent can. Therefore, larger samples can be used thereby greatly increasing the sensitivity of the test.

In use, the unit is mounted on a mounting means. The membrane will have been impregnated with a receptor to a ligand that is to be tested for. For example, in a pregnancy test, the membrane will have been impregnated with anti-HCG. The sample solution can be either a urine sample or a blood serum sample. After the fluid has been contacted with the membrane and withdrawn into porous filter member, a second labeled antibody is contacted with the membrane. If the ligand is present, it will be bound to the first receptor on the surface of the membrane. The bound ligand then acts as a receptor and binds a second, labeled receptor. This is sometimes referred to in the art as a "forward sandwich" assay. See for example, U.S. Pat. No. 4,376,110 issued David et al. If the antigen is present, then the label will be present on the surface of the membrane. The label can be a radiometric, a fluormetric label, and enzymatic label, a colorometric label, or any of a number of other labels well known in the art. It will be appreciated that the present invention is not limited to sandwich assays, but is general for other heterogeneous assays known in the art.

One advantage of the device of the present invention is that tests can be run on a wide variety of compounds in fluids. For example, if the pH of water is to be tested in the device of the present invention, the membrane could be litmus paper. Other similar non-antibody tests will immediately suggest themselves to the skilled artisan. Of course, the preferred tests are antibody tests. The device of the present invention can facilitate tests for a wide range of antigens. A great advantage of the device is that different fluids can be tested for. For example, blood serum and urine can both be tested in the same unit.

Of course, almost any antigen can be analyzed for using the apparatus of the present invention. For example, one can test for HGC, for viral infections such as AIDS or herpes, drugs of abuse such as cocaine or heroin, difficult to diagnose bacterial diseases such as chlamydia or asymptomatic gonorehea, and other antigens.

In a preferred embodiment, at least two different antibodies are present on the membrane, for example, anti-HCG and anti-horseradish peroxidase. The first antibody tests for the presence of the antigen. The second can test if the reagents are working properly, that is, it should always be a positive test if the reagents are added in the correct order. When colorometric labels are used, the two antibodies can be placed on the membrane to form a pattern. For example, a minus if the test is negative, or a plus if the test is positive, or a ring and an inner dot forming a bullseye pattern if the test is positive, and a ring if the test is negative. The membrane is impregnated using the apparatus of U.S. Pat. No. 4,748,042.

The embodiments described are the currently preferred embodiments, but the scope of the invention should not be considered limited by anything other than the appended claims.

I claim:

1. A device for performing immunoassays on analytes comprising:

an immunosorbent membrane;

a means for absorbing liquid, said immunosorbent membrane and said means for absorbing liquid being spaced apart in a first position with said immunosorbent membrane, spaced above said means for absorbing liquid, thereby creating an air gap therebetween, said means for absorbing liquid and said immunosorbent membrane being movable to a second position wherein said immunosorbent membrane substantially contacts said means for absorbing liquid, thereby allow liquid to be drawn through said immunosorbent member and into said means for absorbing liquid; and a piston means located below said means for absorbing liquid, said piston means being movable from a first position to a second position in order to reduce air pressure in said air gap, and thereby aid in drawing analytes through said membrane, past said air gap, and into said means for absorbing liquid.

2. The device of claim 1, wherein said means for absorbing liquid is a porous hydrophilic body.

3. The device of claim 1, wherein said means for absorbing liquid is finely divided desiccant powder.

4. The device of claim 1, wherein said finely divided desiccant powder is supported by a retaining screen.

5. The device of claim 4, wherein said immunosorbent membrane is secured to within a cap by a retaining ring, and said cap is snap fit to a body member.

6. The device of claim 5, wherein said means for absorbing liquid and said membrane are brought into contact with each other by moving said absorbing liquid means upwardly to contact said membrane.

7. The device of claim 5, wherein said body member has a first cap engageable snap fit ring and a second cup engageable snap fit ring.

8. The device of claim 7, wherein said means for absorbing liquid and said membrane are brought into contact with each other by moving said cap downwardly on said body member, said cap thereby moving from a position wherein it is held by said first cap engageable snap fit ring to a position wherein it is held by said second cap engageable snap fit ring.

9. A device for performing immunoassays on analytes comprising:
   an immunosorbent membrane;
   a means for absorbing liquid comprising a finely divided desiccant powder, said immunosorbent membrane and said means for absorbing liquid being arranged in a first position with an air gap formed therebetween, said immunosorbent membrane and said means for absorbing liquid being movable to a second position by moving said means for absorbing liquid upwardly wherein they are in substantial contact, thereby allowing the analyte to be drawn through said immunosorbent membrane and into said means for absorbing liquid; and
   a piston means located below said means for absorbing liquid, said piston means being movable upwardly in order to move said means for absorbing liquid into contact with said membrane from said first position to said second position and thence downwardly in order to reduce air pressure in said air gap, and thereby aid in drawing analytes through said membrane, past said air gap and into said means for absorbing liquid.

10. A device for performing immunoassays on analytes comprising:
    an immunosorbent membrane;
    a means for absorbing liquid comprising a finely divided desiccant powder, said immunosorbent membrane and said means for absorbing liquid being arranged in a first position with an air gap formed therebetween, said immunosorbent membrane and said means for absorbing liquid being movable to a second position by moving said immunosorbent membrane downwardly wherein they are in substantial contact, thereby allowing the analyte to be drawn through said immunosorbent membrane and into said means for absorbing liquid; and
    a piston means located below said means for absorbing liquid, said piston means being movable downwardly in order to reduce air pressure in said air gap, and thereby aid in drawing analytes through said membrane, past said air gap and into said means for absorbing liquid.

* * * * *